United States Patent [19]

Omietanski et al.

[11] 4,033,990

[45] July 5, 1977

[54] HYDROXYBICYCLOSILOXANE RIGID URETHANE FOAM STABILIZERS

[75] Inventors: George M. Omietanski, Marietta, Ohio; Harold D. Furbee, Sistersville, W. Va.; Vincent T. Chuang, Marietta, Ohio

[73] Assignee: Union Carbide Corporation, New York, N.Y.

[22] Filed: Dec. 29, 1972

[21] Appl. No.: 319,788

[52] U.S. Cl. .................. 260/448.2 B; 260/2.5 AH; 260/448.2 E
[51] Int. Cl.$^2$ ............................................ C07F 7/08
[58] Field of Search .............. 260/448.2 B, 448.2 E

[56] References Cited

UNITED STATES PATENTS

| 2,819,245 | 1/1958 | Shorr | 260/448.2 B X |
| 2,823,218 | 2/1958 | Speier et al. | 260/448.2 E |
| 2,924,587 | 2/1960 | Shorr | 260/448.2 B X |
| 2,924,588 | 2/1960 | Shorr | 260/448.2 B X |

*Primary Examiner*—Paul F. Shaver
*Attorney, Agent, or Firm*—Eugene C. Trautlein

[57] ABSTRACT

This application relates to certain novel hydroxybicyclosiloxanes that are particularly useful as foam stabilizers for rigid polyurethane foams. The novel hydroxybicyclosiloxanes have critical siloxane molecular weights and are produced by an addition reaction involving hydrosiloxanes and olefinically unsaturated bicyclic alcohols that contain an olefinic bond which does not shift significantly during the reaction.

9 Claims, No Drawings

HYDROXYBICYCLOSILOXANE RIGID URETHANE FOAM STABILIZERS

Rigid polyether polyurethane foams are produced commercially by introducing several starting materials (i.e., a silicone surfactant, a polyether polyol, a fluorocarbon blowing agent, a catalyst and a polyisocyanate) into a reaction zone. It is important that the relative amounts of the starting materials in the reaction zone be carefully controlled in order to produce a satisfactory polyurethane foam. Control of the relative amount of the starting materials in the reaction zone is achieved, in part, by forming premixtures containing carefully controlled amounts of the silicone surfactant (i.e., a siloxane-polyoxyalkylene block copolymer), polyol, and fluorocarbon. It is desirable that the various components in these premixtures be compatible so as to eliminate the need for stirring the premixtures to insure homogeneity. Certain silicone surfactants are more compatible with the other starting materials in the premixtures than are other silicone surfactants. In particular, those silicone surfactants wherein the polyoxyalkylene blocks are endblocked by hydroxyl groups are generally more compatible in premixtures than are silicone surfactants wherein the polyoxyalkylene blocks are endblocked by alkoxy groups.

Siloxane-polyoxyalkylene block copolymers wherein the polyoxyalkylene blocks are endblocked by hydroxyl groups are often prepared by the addition of a linear polyoxyalkylene polymer endblocked at one end by an allyl group and at the other end by a hydroxyl group (or a group convertible to a hydroxyl group) with a hydrosiloxane. Such polyoxyalkylene reactants can be produced by reacting allyl alcohol with one or more alkylene oxides followed, if desired, by converting the hydroxy group to a group convertible to a hydroxyl group. In the addition reaction, the SiH groups add to the allyl group to produce the block copolymer. When the polyoxyalkylene reactant contains an alcoholic hydroxyl endblocking group, such groups can also react to some extent with SiH groups thereby decreasing the content of the desired hydroxyl groups in the block copolymer product with a resulting decrease in the compatibility of the block copolymer in the above-mentioned premixtures. This side reaction also undesirably increases the viscosity of the block copolymer product by partially crosslinking the block copolymer. Further, during the addition reaction, endblocking allyl groups in the polyoxyalkylene reactant tend to isomerize to some extent to propenyl groups which can react with the hydroxyl endblocking groups of the polyoxyalkylene reactant or block copolymer to form acetal groups. These side reactions also reduce the premixture compatability of the block copolymer by decreasing its hydroxyl content and also lead to an undesirable viscosity increase in the block copolymer by partially crosslinking the block copolymer.

When the polyoxyalkylene reactant contains an endblocking group convertible to a hydroxyl group, the undesirable side reactions of the hydroxyl group with the SiH groups and propenyl groups do not occur but the undesirable isomerization of allyl groups can still occur and the block copolymer initially formed must be further processed to regenerate the hydroxyl groups.

It is an object of this invention to provide hydroxybicyclosiloxanes that are useful as foam stabilizers for rigid polyether polyurethane foams.

It is an object of this invention to provide hydroxybicyclosiloxanes that are useful as foam stabilizers for rigid polyether polyurethane foams and that are readily produced from relatively simple alcohol reactants.

It is an object of this invention to provide hydroxybicyclosiloxanes that are useful as foam stabilizers for rigid polyether polyurethane foams and that are produced by a process relatively free of undesirable side reactions.

Other objects of this invention will be apparent from the description thereof appearing below.

This invention provides hydroxybicyclosiloxanes consisting essentially of: (A) at least one hydroxybicyclosiloxane unit having the formula:

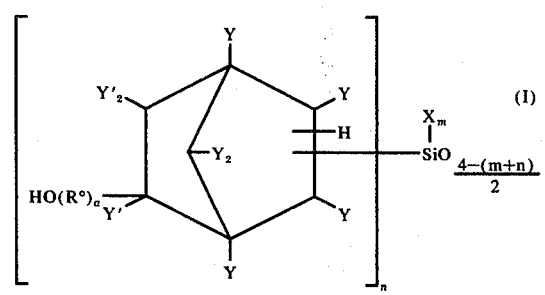

wherein Y is hydrogen or an alkyl group containing from 1 to 4 carbon atoms inclusive, Y' is hydrogen or an alkyl group containing from 1 to 12 carbon atoms inclusive, R° is a divalent hydrocarbon group free of aliphatic carbon to carbon multiple bonds, $a$ has a value of 0 or 1, X is a monovalent hydrocarbon group free of aliphatic carbon to carbon multiple bonds, $m$ has a value of 0, 1 or 2, $n$ has a value of 1 or 2 (preferably 1), and $(m+n)$ has a value of 1, 2 or 3, each hydroxybicyclosiloxane group has no more than 20 (preferably no more than 10) carbon atoms; and (B) at least three hydrocarbylsiloxane units represented by the formula:

wherein $p$ has a value of 1, 2 or 3 and Z is a monovalent hydrocarbon group free of aliphatic carbon to carbon mutliple bonds, the molecular weight of the siloxane portion of the hydroxybicyclosiloxane being from about 250 to about 1300 inclusive, and, when dihydrocarbylsiloxane units ($Z_2SiO$ units) are present, the ratio of hydroxybicyclosiloxane units to dihydrocarbylsiloxane units is at least 0.5 to 1.0. Preferably, the siloxane portion represents from 50 to 80 weight percent of the hydroxybicyclosiloxane. As used herein, the "siloxane portion" of the hydroxybicyclosiloxane includes all of the groups and atoms in the hydroxybicyclosiloxane apart from the hydroxybicyclo groups, i.e., apart from the groups in the brackets in formula (I).

A preferred class of the hydroxybicyclosiloxanes of this invention are represented by the average formula:

wherein X° is

-continued

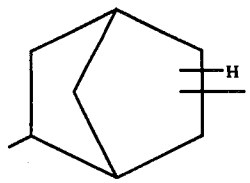

or

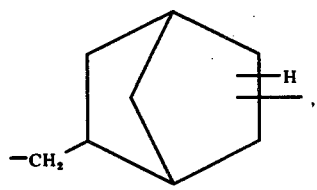

Me is a methyl group, x has a value from 1 to 8 inclusive, y has a value from 1 to 6 inclusive, the molecular weight of the hydroxybicyclosiloxane, exclusive of the hydroxybicyclo groups (i.e., the HOX° — groups), is from about 300 to about 1000 inclusive and x:y is at least 0.5:1.

Typical of the monovalent hydrocarbon groups free of aliphatic carbon to carbon to carbon multiple bonds represented by X and Z in formulas (I) and (II) above are the alkyl groups (for example, the methyl, ethyl, n-propyl, iso-propyl, n-butyl, sec-butyl, isobutyl, t-butyl, n-octyl, decyl, dodecyl groups), the cycloalkyl groups (for example, the cyclopropyl, cyclobutyl, cyclopentyl, cyclohexyl, cycloheptyl groups), the aryl groups (for example, the phenyl, naphthyl, phenathrenyl, anthracenyl groups), the aralkyl groups (for example, the benzyl, 2-phenylethyl, 2-phenylpropyl, cumyl groups), the alkaryl groups (for example, the tolyl, t-butylphenyl, cyclohexylphenyl groups). X and Z are preferably methyl groups. Typical of the divalent hydrocarbon groups represented by R° in formula (I) above are the methylene, ethylene, 1,2-propylene, 1,3-propylene, butylene, phenylene and tolylene groups. Typical of the alkyl groups represented by Y are the methyl, ethyl, propyl and butyl groups and typical of the alkyl groups represented by R' are the methyl, ethyl, propyl, butyl, pentyl, hexyl, decyl and dodecyl groups. Preferably, Y and Y' are hydrogen.

This invention still further provides a process for producing the hydroxybicyclosiloxanes described above which process comprises reacting (1) an olefinic bicyclic alcohol represented by the formula:

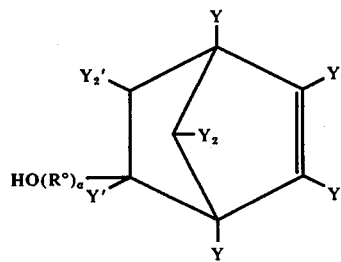

(IV)

wherein the symbols are as defined for formula (I) with (2) a hydrosiloxane consisting essentially of (A) at least one siloxane unit having the formula:

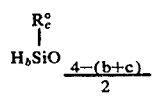

(V)

wherein the symbols are as defined for formula (I), and (B) at least three units having formula (II) above, the molecular weight of the hydrosiloxane being from 250 to 1300 inclusive, in the presence of (3) a catalyst for the addition of SiH to olefinic bonds. When hydroxybicyclosiloxanes of this invention containing dihydrocarbysiloxane units are produced, the hydrosiloxane reactant must have a ratio of hydrosiloxane units to dihydrocarbylsiloxane units of at least 0.5 to 1.

Typical olefinic bicyclic alcohols that are useful in producing the hydroxybicyclosiloxanes of this invention are disclosed in copending U.S. patent application Ser. No. 218,595, filed Jan. 17, 1972 now U.S. Pat. No. 3,798,253.

The hydrosiloxane reactants used to produce the hydroxybicyclosiloxanes of this invention can be produced by cohydrolyzing and cocondensing the appropriate hydrolyzable silanes or by equilibrating appropriate siloxanes using conventional techniques.

The process for producing the hydroxyhydrobicyclosiloxanes of this invention is conducted in the same manner as used in producing known hydrosiloxane olefinic compound adducts (i.e., at elevated temperatures and in the presence of a catalyst). Since relatively little side reactions occur, approximately stoichiometric amounts of the olefinic alcohol and the hydrosiloxane (one olefinic group per SiH group) can be employed. Solvents for the alcohol and hydrosiloxane reactants (e.g., liquid hydrocarbons such as toluene) can be employed. Amounts of platinum catalysts that provide from 10 to 200 parts by weight of platinum per million parts by weight of the reactants are useful. Suitable reaction temperatures are from 50° C. to 100° C. Suitable addition catalysts include chloroplatinic acid and complexes thereof and elemental platinum supported on charcoal or gamma alumina. If desired, the process can be conducted at a basic pH which may further reduce the possibility of side reactions. To this end, an amine (e.g., triethyl amine) can be included in the reaction mixture. At the conclusion of the process, any residual (unreacted) SiH can be removed by adding a small amount of methanol and sodium bicarbonate to the product and heating.

In view of the fact that the olefinic bonds in the alcohol reactants used in producing the siloxanes of this invention do not isomerize significantly during the reaction with hydrosiloxanes and do not undergo other side reactions significantly, the resulting product contains little undesirable by products. Another advantage of this process is that it involves the use of monomeric alcohol reactants as distinguished from the polyoxyalkylene alcohol reactants employed in prior art processes. Further, the monomeric alcohol reactants employed in the process of this invention need not be reacted to block the hydroxy groups as is done in some prior art processes involving the use of polyoxyalkylene alcohol reactants.

This invention also provides a method for producing rigid polyurethane foams by reacting and foaming a foam formulation (reaction mixture) comprising (a) a polyether containing at least two hydroxyl groups and having a hydroxyl number from about 200 to about 1000, (b) an organic polyisocyanate, (c) a catalyst for the reaction of (a) and (b) to produce the polyurethane, (d) a blowing agent and (e) a novel hydroxybicyclosiloxane as described above as a foam stabilizer.

The polyethers that are useful in producing rigid polyurethane foam in accordance with this invention include polyoxyalkylene polyols including alkylene oxide adducts of, for example, glycerol, 1,2,6-hexanetriol, 1,1,1-trimethylolethane, 1,1,1-trimethylolpropane, pentaerythritol, sorbitol, sucrose, lactose, alpha-methylglucoside, alpha-hydroxy-alkylglucoside, ammonia, triethanolamine, triisopropanolamine, ethylenediamine, diethylenetriamine, novolac resins, phosphoric acid, benzenephosphoric acid, polyphosphoric acids such as tripolyphosphoric acid and tetrapolyphosphoric acid, phenol-aniline-formaldehyde ternary condensation products, aniline-formaldehyde condensation products, and the like, are useful. The alkylene oxides employed in producing polyoxyalkylene polyols normally have from 2 to 4 carbon atoms. Propylene oxide and mixtures of propylene oxide with ethylene oxide are preferred.

The hydroxyl number of the polyether polyols in producing polyurethane foams in accordance with this invention can range from about 200 to about 1000. The hydroxyl number is defined as the number of milligrams of potassium hydroxide required for the complete neutralization of the hydrolysis product of the fully acetylated derivative prepared from 1 gram of polyol. The hydroxyl number can also be defined by the equation:

$$OH = \frac{56.1 \times 1000 \times f}{m.w.}$$

where
OH=hydroxyl number of the polyol
$f$=average functionality, that is, average number of hydroxyl groups per molecule of polyol
m.w.= average molecular weight of the polyol.

The organic polyisocyanates that are useful in producing polyurethane foams in accordance with this invention are organic compounds that contain at least two isocyanato groups. Suitable organic polyisocyanates include the poly(aryleneisocyanates) and the hydrocarbon diisocyanates, (e.g., the alkylene diisocyanates and the arylene diisocyanates).

Illustrative of suitable polyisocyanates are
1,2-diisocyanatoethane,
1,3-diisocyanatopropane,
1,2-diisocyanatopropane,
1,4-diisocyanatobutane,
1,5-diisocyanatopentene,
1,6-diisocyanatohexane,
bis(3-isocyanatopropyl)ether,
bis(3-isocyanatopropyl) sulfide,
1,7-diisocyanatoheptane,
1,5-diisocyanato-2-dimethylpentane,
1,6-diisocyanato-3 methoxyhexane,
1,8-diisocyanatooctane,
1,5-diisocyanato-2,2,4-trimethylpentane,
1,9-diisocyanatononane,
1,10-di(isocyanatopropyl)ether of 1,4-butylene glycol,
1,11-diisocyanatoundecane,
1,12-diisocyanatododecane,
bis(isocyanatohexyl)sulfide,
1,4-diisocyanatobenzene,
2,4-diisocyanatotoluene,
2,6-diisocyanatotolylene,
1,3-diisocyanato-o-xylene,
1,3-diisocyanato-m-xylene,
1,3-diisocyanato-p-xylene,
2,4-diisocyanato-1-chlorobenzene,
2,4-diisocyanato-1-nitrobenzene, and
2,5-diisocyanato-1-nitrobenzene.

Suitable poly(aryleneisocyanates) include polymethylene poly(phenyleneisocyanates) having the formula:

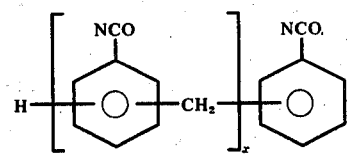

wherein $x$ has an average value from 1.1 to 5 inclusive (preferably from 2.0 to 3.0).

The catalysts that are useful in producing polyurethane foams in accordance with this invention include amine catalysts and metal catalysts. Useful amine catalysts include tertiary amines such as N,N-dimethyl-2-[2-dimethylaminoethoxy]ethylamine, trimethylamine, N-methylmorpholine, N-ethylmorpholine, N,N-dimethylbenzylamine, N,N-dimethylethanolamine, N,N,N',N'-tetramethyl-1,3-butanediamine, triethanolamine, 1,4-diazabicyclo[2,2,2]octane (triethylenediamine), hexadecyldimethylamine, and the like. Useful metal catalysts include dibutyl tin dilaurate.

Blowing agents that are useful in producing polyurethane foam in accordance with this invention include water, halogenated hydrocarbons (e.g., fluorocarbons) such as trichloromonofluoromethane, dichlorodifluoromethane, dichloromonofluoromethane, dichloromethane, trichloromethane, 1,1-dichloro-1-fluoroethane, 1,1,2-trichloro-1,2,2-trifluoromethane, hexafluorocyclobutane, octafluorocyclobutane, and the like. Another class of blowing agents include thermally-unstable compounds which liberate gases upon heating, such as N,N'-dimethyl-N,N'-dinitrosoterephthalamide and the like.

The relative amounts of the various components used in producing polyurethane foams in accordance with this invention are not narrowly critical. The polyether polyol and the polyisocyanate, taken together, are present in the foam formulations (reaction mixtures) used to produce such foams in a major amount. The relative amounts of these two components is the amount required to produce a polyurethane structure of the foam and such relative amounts are well known in the art. The blowing agent and catalyst are each present in the known amount necessary to achieve the function of the component. Thus, the blowing agent is present in a minor amount sufficient to foam the reaction mixture to the desired density and the catalyst is present in a catalytic amount (i.e., an amount sufficient to catalyze the reaction to produce the polyurethane at a reasonable rate). The siloxane is present in a foam-stabilizing amount (i.e., in an amount sufficient to stabilize the foam). The siloxane is preferably employed in an amount of from 0.2 to 5.0 parts by weight per 100 parts by weight of the polyol, polyisocyanate, catalyst and siloxane.

Conventional additives can be employed in minor amounts in producing polyurethane foams in accordance with the process of this invention if desired for specific purposes. Such additives include inhibitors (such as alpha-methyl styrene and alloocimene) and flame retardants (such as "FYROL-6").

If desired, mixtures of the above-described starting materials (i.e., polyols, polyisocyanates, etc.) can be used in producing polyurethane foams in accordance with this invention.

In accordance with this invention, polyurethane foams are produced by the conventional procedures such as the one-step or one-shot technique wherein all of the reactants are reacted simultaneously with the foaming operation. The foaming and the urethane-forming reaction in the one-step technique occur without the application of external heat. Thereafter, the foam can be heated (postcured) at 150° F. to 212° F. to eliminate any surface tackiness if desired. Preferred novel siloxanes and premixtures containing the novel siloxanes are of low viscosity and do not present particular problems when pumped into mixing headings in the technique conventionally used in the one-shot process. It is often convenient to prepare premixtures containing the hydroxybicyclosiloxane, the blowing agent and the polyol. Such premixtures can also contain the catalysts and/or other additives.

The rigid polyurethane foams produced in accordance with this invention can be used for the same purposes as conventional rigid polyether polyurethane foams (e.g., they can be used as thermal insulating materials in buildings and in refrigerators).

The hydroxybicyclosiloxanes of this invention are also useful as lubricants for textile fibers, emulsifiers and wetting agents.

In the above formulas, the symbols representing the numbers and types of groups need not have the same meaning at each occurrence throughout the composition. For example, some of the groups represented by formula (II) above can be dimethylsiloxane ($Me_2SiO$) while other of such groups can be triethylsiloxane ($[C_2H_5]_3SiO_{0.5}$).

Other hydroxy-organosiloxane rigid polyurethane foam stabilizers are disclosed in U.S. patent application No. 319,786, now U.S. Pat. No. 3,842,112 filed concurrently herewith in the names of G. M. Omietanski and V. T. Chuang, entitled "Hydroxyalkenylsiloxane Rigid Urethane Foam Stabilizers" and in U.S. patent application Ser. No. 319,528, now U.S. Pat. No. 3,879,433 filed concurrently herewith in the names of G. M. Omietanski and V. T. Chuang entitled "Hydroxyalkylsiloxane Rigid Urethane Foam Stabilizers."

The following Examples illustrate the present invention.

In the following Examples, the abbreviations and symbols used have the indicated meanings:

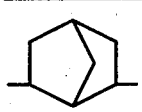
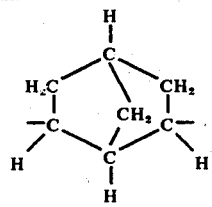

| | |
|---|---|
| cc | cubic centimeters |
| cstks | viscosity in centistokes at 25° C. |
| Et | ethyl |
| "FYROL-6" | Diethyl-bis(2-hydroxyethyl)amine methylphosphonate |
| g. | grams |
| gal. | gallon |
| I.R. | infra red |
| lbs. | pounds |
| Me | methyl |
| min. | minute |
| ml. | milliliter |
| MW | molecular weight |
| NMR | Nuclear Magnetic Resonance |
| % | percent |
| "PAPI" | A polymeric polyisocyanate having the average formula: |

$$H \left[ \begin{array}{c} NCO \\ | \\ \bigcirc \end{array} - CH_2 \right]_x \begin{array}{c} NCO \\ | \\ \bigcirc \end{array}$$

where x has an average value of 1.7

| | |
|---|---|
| Polyol I | A polypropylene oxide triol having a hydroxyl number of 450 produced by reacting sucrose with propylene oxide |
| ppm | parts by weight per million parts by weight |
| psig | pounds per square inch gauge pressure |
| sparge | Denotes passing a gas (e.g., nitrogen) through the liquid. |
| TMBDA | N,N,N',N'-tetramethyl-1,3-butanediamine. |
| "UCON-11" | trichloromonofluoromethane |

Hydrosiloxane Preparation

The following procedure is illustrative of a method that can be employed in making the hydrosiloxane reactants useful in producing the hydroxybicyclosiloxanes of this invention. A solution of 0.0168 moles of a hydrosiloxane having the nominal formula $Me_3SiO(MeHSiO)_{40}SiMe_3$ (43.0g, 354cc/g SiH), 0.959 moles of a mixture of hexamethylcyclotrisiloxane and octamethylcyclotetrasiloxane (70.9) and 0.223 moles of hexamethyldisiloxane (36.1g, 99.8%) were reacted in the presence of 3.0g sulfuric acid (reagent grade) for 4 hours. This solution was then neutralized with sodium bicarbonate and filtered to give a water white clear equilibrated filtrate with a "nominal" formula of $Me_3SiO(Me_2SiO)_4(MeHSiO)_{2.8}SiMe_3$, a viscosity of 4.2 centistokes and a silanic hydrogen content of 102cc/g. The above-described reactions were carried out in a 500 ml, three-necked round bottom Morton flask equipped with a stirrer and two glass stoppers. The above nominal formula for this hydrosiloxane is the theoretical formula calculated on the basis of complete reaction of the siloxane starting materials. In this instance, the nominal formula is in agreement with the experimentally measured silanic hydrogen content of the hydrosiloxane. In the case of those of the hydrolsiloxanes described below where the experimentally measured silanic hydrogen contents did not agree with the nominal formulas, the nominal formulas were corrected to agree with the silanic hydrogen measurement and the corrected formulas appear below.

Catalyst Solutions

The chloroplatinic acid used in producing the hydroxybicyclosiloxanes described below was employed in the form of a solvent solution. The solution contained 3.3 or 10 parts by weight of chloroplatinic acid hexahydrate and 96.7 or 90 parts by weight of a mixture of solvents. The mixture of solvents consisted of 90 weight percent of the dimethyl ether of ethylene glycol and 10 weight percent of ethanol.

EXAMPLE I

A solution of 0.214 moles of 2-hydroxymethylbicycloheptene-5 (27.2 g, 97.8% purity) and a hydrosiloxane with the average formula of $Me_3SiO(Me_2SiO)_4$-$(MeHSiO)_{2.8}SiMe_3$ (0.161 equivalents of SiH, 35.3 g 102 cc/g SiH, 4.2 cstks) were reacted in the presence of chloroplatinic acid solution (100 parts by weight of platinum per million parts by weight of reactants) and 0.3 gram $Et_3N$ (0.5 wt-% based on reactants). The resultant adduct had an average formula of

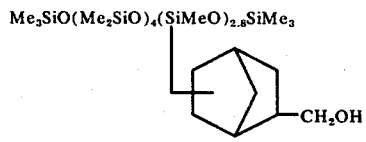

and a viscosity of 4,607 cstks. The reaction was carried out in a 250 ml, 3-necked round-bottom flask fitted with a stirrer, thermometer, Dean Stark trap, sparge tube and a condenser. The reaction solution, under nitrogen sparge, was mixed, heated to 60° C and catalyzed. Additional controlled heating at 80°–100° C was maintained until the hydrosilylation was completed (as evidenced by the absence of hydrogen in the silicon hydride alcoholic KOH fermentation tube test). The siloxane portion of the adduct

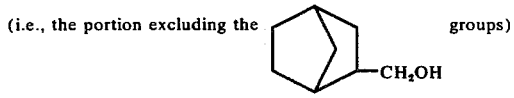

has a molecular weight of 623 and the siloxane content of the adduct was 54 weight percent. A solution containing 70 weight percent of this adduct and 30 weight percent of toluene had a viscosity of 38 centistokes at 25° C. This viscosity reduction by addition of a solvent indicates that the high bulk viscosity of the adduct is not due to cross-linking but rather is due to hydrogen bonding.

EXAMPLE II

Using the procedure described in Example I, 0.091 moles of 5-norbornen-2-ol (10.0 g) and a hydrosiloxane with an average formula of $Me_3SiO(Me_2SiO)_4$-$(MeHSiO)_{2.8}SiMe_3$ (0.086 equivalents of SiH, 18.9 g, 102 cc/g, 4.2 cstks) were reacted in the presence of 0.12 ml of 3.3 wt-% chloroplatinic acid solution (50 parts by weight of platinum per million parts by weight of reactants) and 0.1 g $Et_3N$ (0.5 wt-% based on reactants), dissolved in 33.5 g of toluene. An additional 0.0046 moles of 5-norbornene-2-ol (0.5 g) and 0.12 ml of the 3.3 wt-% chloroplatinic acid solution were used to drive the hydrosilylation to completion. The toluene was then removed from the solution at 140° C under a nitrogen sparge. The resulting adduct is represented by the average formula

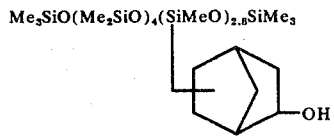

and had a viscosity of 3,555 cstks. The siloxane portion of the adduct had a molecular weight of 623 and the siloxane content of the adduct was 64 weight percent.

EXAMPLE III

The siloxanes produced as described in Examples I and II above were used in producing polyurethane foams using the formulation and foaming procedure described below.

| Formulation Material | Parts by Weight | |
|---|---|---|
| Polyol 1 | 70.0 | |
| "FYROL-6" | 30.0 | |
| "UCON-11" | 50.0 | |
| TMBDA | 1.5 | |
| Hydroxybicyclosiloxane | 0.2 | or 0.4 |
| "PAPI" (Index 105) | 110.0 | |

Foaming Procedure

A cleaned and waxed mold was heated to 212° F. and any excess wax was removed with a clean cloth. A premixture was formed containing the "FYROL-6," Polyol I, TMBDA and "UCON 11." The premixture was thoroughly mixed until completely homogeneous and any UCON 11 that volatilized during mixing was replaced. The mold is cooled to about 120° F. The siloxane is added to the premixture and the premixture is again mixed for 10 seconds. Then the "PAPI" is added to the premixture and the resulting formulation is mixed for 8 seconds. The formulation is introduced into the mold which is then closed. The temperature of the mold is maintained at 115° to 125° F. for 5 minutes. Then the mold is placed into a 212° F. oven for 5 minutes. The cured foam is then removed from the mold. A slice is cut from the center of the foam and the number of cells per linear inch in the middle of the slice is measured. The latter measurement is an index of the fineness of the cell structure. A foam having fewer than 26 cells per inch is regarded as unsatisfactory ("coarse"). The "Rise" or height of the foam is measured. In view of the fact that the formulation used to produce the foam is viscous, a portion thereof sticks to the walls of the container in which the formulation is formed when the bulk of the formulation is introduced into the mold. Accordingly, the foam is weighed and the measured rise is corrected to allow for the amount of the formulation retained in the container by using the following formula:

Corrected Rise =

$$\left[ 10 \times \frac{\text{formulation weight}}{\text{foam weight}} - 10 \right] + [\text{Measured Rise}]$$

Corrected Rise values are reported below. The Rise of a foam is roughly proportional to the potency of the foam stabilizer used to produce the foam.

Premixture Compatibility Test

A mixture is formed containing the following materials:
840 grams Polyol I
360 grams FYROL-6
18 grams TMBDA 600 grams UCON-11

The mixture is stirred at moderate speed with an air motor equipped with a 2-inch propeller. Any UCON-11 that evaporates during the mixture is replaced by adding more UCON-11 to the mixture. A 75.8 gram sample of the mixture so formed is added to a jar and then 0.5 cubic centimeters of a hydroxybicyclosiloxane is added to the jar to form a premixture. The premixture is maintained at a temperature below 23° C to minimize loss of UCON-11 by volatilization. The premixture is stirred with a spatula until well mixed and is then observed visually for clarity or opaqueness.

The results of the above foam preparations are shown in Table I below:

TABLE I

| Product From | Premixture Compatibility | Foam Properties | | |
|---|---|---|---|---|
| | | Parts of Product | Rise (In.) | Cell (In.) |
| Example I | Clear | 0.4 | 22.9 | 42 |
| | | 0.2 | 17.6 | 30 |
| Example II | Clear | 0.4 | 16.2 | 34 |
| | | 0.2 | 13.5 | coarse |
| * | Clear | 0.2 | 18.0 | 35 |

*A commercially available siloxane-polyoxyalkylene block copolymer rigid polyether polyurethane foam stabilizer. Not a hydroxybicyclosiloxane of this invention. Presented only for purposes of comparison.

What is claimed is:

1. A hydroxybicyclosiloxane consisting essentially of: (A) at least one hydroxybicyclosiloxane unit having the formula:

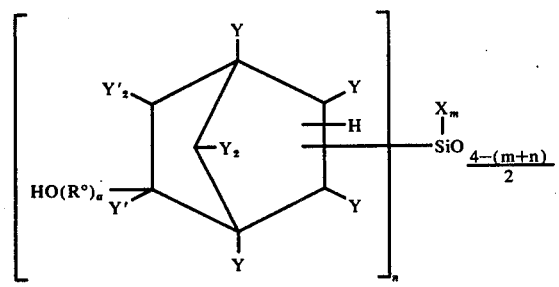

wherein Y is hydrogen or an alkyl group containing from 1 to 4 carbon atoms inclusive, Y' is hydrogen or an alkyl group containing from 1 to 12 carbon atoms inclusive, R° is a divalent hydrocarbon group free of aliphatic carbon to carbon multiple bonds, $a$ has a value of 0 or 1, X is a monovalent hydrocarbon group free of aliphatic carbon to carbon multiple bonds, $m$ has a value of 0, 1 or 2, $n$ has a value of 1 or 2, and ($m+n$) has a value of 1, 2 or 3, each hydroxybicyclosiloxane group has no more than 20 carbon atoms; and (B) at least hydrocarbylsiloxane units represented by the formula:

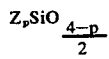

wherein $p$ has a value of 1, 2 or 3 and Z is a monovalent hydrocarbon group free of aliphatic carbon to carbon multiple bonds, the molecular weight of the siloxane portion of the hydroxybicyclosiloxane being from about 250 to about 1300 inclusive, and, when dihydrocarbylsiloxane units ($Z_2SiO$ units) are present, the ratio of hydroxybicyclosiloxane units to dihydrocarbylsiloxane units is at least 0.5 to 1.0.

2. A hydroxybicyclosiloxane as claimed in clam 1 wherein each hydroxybicylcosiloxane group has no more than 10 carbon atoms and the siloxane portion represents from 60 to 80 weight percent of the hydroxybicyclosiloxane.

3. A hydroxybicyclosiloxane as claimed in claim 1 containing at least one hydroxybicyclosiloxane unit as defined in claim 1 wherein $m+n$ is 1.

4. A hydroxybicyclosiloxane as claimed in claim 1 containing at least one hydroxybicyclosiloxane unit as defined in claim 1 wherein $m+n$ is 2.

5. A hydroxybicyclosiloxane as claimed in claim 1 represented by the average formula:

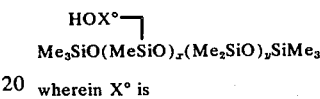

wherein X° is

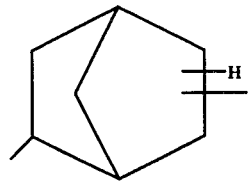

or

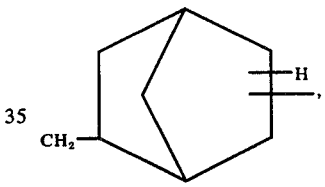

Me is a methyl group, $x$ has a value from 1 to 8 inclusive, $y$ has a value from 1 to 6 inclusive, the molecular weight of the hydroxybicyclosiloxane exclusive of the hydroxybicyclo groups is from about 300 to about 1000 inclusive and $x:y$ is at least 0.5:1.

6. A process for producing a hydroxybicyclosiloxane as claimed in claim 1 which process comprises reacting (1) an olefinic bicyclic alcohol represented by the formula:

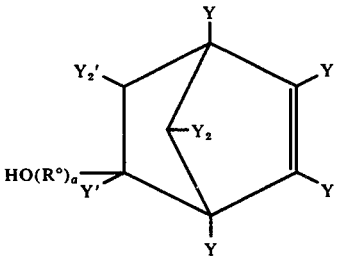

wherein the symbols are as defined in claim 1 with (2) a hydrosiloxane consisting essentially of (A) at least one siloxane unit having the formula:

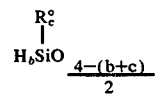

wherein the symbols are as defined in claim 1 and (B) at least three hydrocarbylsiloxane units as defined in claim 1 above, the molecular weight of the hydrosiloxane being from 250 to 1300 inclusive and, when a hydroxybicyclosiloxane containing dihydrocarbylsiloxane units is being produced, the ratio of hydrosiloxane units to dihydrocarbylsiloxane units in the hydrosiloxane is at least 0.5 to 1 in the presence of (3) a catalyst for the addition of SiH to olefinic bonds.

7. A process as claimed in claim 6 wherein the alcohol is present in an amount that provides about 1 olefinic group per SiH of the hydrosiloxane.

8. A process as claimed in claim 6 wherein the catalyst is a platinum catalyst.

9. A process as claimed in claim 6 wherein the catalyst is chloroplatinic acid.

* * * * *

UNITED STATES PATENT OFFICE
CERTIFICATE OF CORRECTION

Patent No. 4,033,990          Dated July 5, 1977

Inventor(s) G. M. Omietanski, H. D. Furbee and V. T. Chuang

It is certified that error appears in the above-identified patent and that said Letters Patent are hereby corrected as shown below:

Col. 3, line 28, delete "to carbon", second appearance

Col. 8, lines 55 & 56, after "the" delete "hydrolsiloxanes" and insert -- hydrosiloxanes --

Col. 12, line 4, after "each", delete "hydroxybicylcosiloxane" and insert -- hydroxybicyclosiloxane --

*Signed and Sealed this*

*Fifteenth* Day of *August 1978*

[SEAL]

Attest:

RUTH C. MASON
*Attesting Officer*

DONALD W. BANNER
*Commissioner of Patents and Trademarks*